(12) United States Patent
Criscuolo et al.

(10) Patent No.: US 9,398,943 B2
(45) Date of Patent: Jul. 26, 2016

(54) VENTRAL HERNIA REPAIR WITH BARBED SUTURE

(75) Inventors: Christopher J. Criscuolo, Branford, CT (US); Jonathan Glick, Hamden, CT (US); Timothy D. Kosa, Hamden, CT (US); Michael Primavera, Orange, CT (US); Kevin Slisz, Old Saybrook, CT (US)

(73) Assignee: Covidien LP, New Haven, CT (US)

( * ) Notice: Subject to any disclaimer, the term of this patent is extended or adjusted under 35 U.S.C. 154(b) by 1210 days.

(21) Appl. No.: 12/943,107

(22) Filed: Nov. 10, 2010

(65) Prior Publication Data
US 2011/0130774 A1    Jun. 2, 2011

Related U.S. Application Data
(60) Provisional application No. 61/264,922, filed on Nov. 30, 2009.

(51) Int. Cl.
*A61F 2/00* (2006.01)

(52) U.S. Cl.
CPC ....... *A61F 2/0063* (2013.01); *A61F 2002/0072* (2013.01)

(58) Field of Classification Search
USPC ........................................ 606/151; 623/23.72
See application file for complete search history.

(56) References Cited

U.S. PATENT DOCUMENTS

| | | | |
|---|---|---|---|
| 3,123,077 A | 3/1964 | Alcamo | |
| 3,646,615 A | 3/1972 | Ness | |
| 4,769,038 A | 9/1988 | Bendavid et al. | |
| 4,979,956 A | 12/1990 | Silvestrini | |
| 5,425,747 A | 6/1995 | Brotz | |
| 5,507,811 A * | 4/1996 | Koike et al. | 606/151 |
| 5,584,859 A | 12/1996 | Brotz | |
| 5,593,441 A | 1/1997 | Lichtenstein et al. | |
| 5,683,417 A | 11/1997 | Cooper | |
| 5,743,917 A | 4/1998 | Saxon | |
| 5,855,619 A | 1/1999 | Caplan et al. | |
| 5,931,855 A | 8/1999 | Buncke | |
| 6,270,517 B1 | 8/2001 | Brotz | |

(Continued)

FOREIGN PATENT DOCUMENTS

| | | |
|---|---|---|
| EP | 2 108 319 A1 | 10/2009 |
| EP | 2 133 028 A1 | 12/2009 |

(Continued)

OTHER PUBLICATIONS

European Search Report for European Application No. 10250002.2 dated Mar. 24, 2010. (9 pages).

(Continued)

*Primary Examiner* — Alexander Orkin

(57) ABSTRACT

The present disclosure is directed to a method and system for the repair of ventral hernias. The method includes the steps of providing a needle; providing a barbed suture having a distal end attached to the needle; providing a surgical mesh; rolling the surgical mesh, the barbed suture, and the needle to form a rolled mesh having the needle oriented substantially parallel to a longitudinal axis of the rolled mesh; transferring the rolled mesh into a body cavity via a laparoscopic device; unrolling and laying the surgical mesh under a ventral hernia in an abdominal wall; threading the needle and barbed suture through the surgical mesh and the abdominal wall; and trimming the barbed suture.

10 Claims, 9 Drawing Sheets

(56) References Cited

U.S. PATENT DOCUMENTS

| | | | |
|---|---|---|---|
| 6,368,356 | B1 | 4/2002 | Zhong et al. |
| 6,383,201 | B1 | 5/2002 | Dong |
| 6,599,323 | B2 | 7/2003 | Melican et al. |
| 6,638,312 | B2 | 10/2003 | Plouhar et al. |
| 6,669,706 | B2 | 12/2003 | Schmitt et al. |
| 6,692,499 | B2 | 2/2004 | Törmälä et al. |
| 6,736,854 | B2 | 5/2004 | Vadurro et al. |
| 6,852,330 | B2 | 2/2005 | Bowman et al. |
| 6,893,452 | B2 | 5/2005 | Jacobs |
| 6,946,003 | B1 | 9/2005 | Wolowacz et al. |
| 7,011,688 | B2 | 3/2006 | Gryska et al. |
| 7,081,135 | B2 * | 7/2006 | Smith et al. ............... 623/8 |
| 7,156,862 | B2 | 1/2007 | Jacobs et al. |
| 7,160,333 | B2 | 1/2007 | Plouhar et al. |
| 7,368,124 | B2 | 5/2008 | Chun et al. |
| 7,371,253 | B2 | 5/2008 | Leung et al. |
| 7,404,819 | B1 | 7/2008 | Darios et al. |
| 7,413,571 | B2 | 8/2008 | Zamierowski |
| 2002/0077661 | A1 | 6/2002 | Saadat |
| 2002/0103494 | A1* | 8/2002 | Pacey ..................... 606/151 |
| 2002/0120348 | A1 | 8/2002 | Melican et al. |
| 2003/0149447 | A1 | 8/2003 | Morency et al. |
| 2004/0010275 | A1 | 1/2004 | Jacobs et al. |
| 2004/0060409 | A1 | 4/2004 | Leung et al. |
| 2005/0113938 | A1 | 5/2005 | Jamiolkowski et al. |
| 2005/0267531 | A1 | 12/2005 | Ruff et al. |
| 2006/0111734 | A1 | 5/2006 | Kaplan et al. |
| 2007/0112361 | A1* | 5/2007 | Schonholz et al. ........... 606/151 |
| 2007/0129811 | A1 | 6/2007 | Plouhar et al. |
| 2008/0077181 | A1 | 3/2008 | Jones et al. |
| 2008/0167519 | A1* | 7/2008 | St-Germain ................ 600/37 |
| 2008/0195121 | A1* | 8/2008 | Eldar et al. ................ 606/151 |
| 2009/0018655 | A1 | 1/2009 | Brunelle et al. |
| 2009/0024226 | A1 | 1/2009 | Lesh |
| 2009/0030526 | A1 | 1/2009 | Sommerich et al. |
| 2009/0082792 | A1* | 3/2009 | Koyfman et al. ........... 606/151 |
| 2009/0216075 | A1* | 8/2009 | Bell et al. ................. 600/37 |
| 2009/0228021 | A1 | 9/2009 | Leung |
| 2010/0069930 | A1 | 3/2010 | Roslin et al. |

FOREIGN PATENT DOCUMENTS

| | | | |
|---|---|---|---|
| WO | WO 2007/047743 | A2 | 4/2007 |
| WO | WO 2008/045375 | A2 | 4/2008 |
| WO | WO 2009/086172 | A2 | 7/2009 |

OTHER PUBLICATIONS

European Search Report for EP 10177651.6-1526 date of completion is Dec. 14, 2010 (3 pages).
European Search Report for EP 10252015.2-2320 date of completion is Mar. 22, 2011 (3 pages).
Canadian Office Action issued May 4, 2016 in corresponding Canadian Patent Application No. 2,721,546, 4 pages.

* cited by examiner

VENTRAL HERNIA REPAIR WITH BARBED SUTURE

CROSS-REFERENCE TO RELATED APPLICATION

The present application claims the benefit of and priority to U.S. Provisional Application Ser. No. 61/264,922, filed on Nov. 30, 2009, the entire disclosure of which is incorporated herein by reference.

BACKGROUND

1. Technical Field

The present disclosure relates to methods and systems for the application of a surgical mesh. More particularly, the present disclosure relates to systems and methods for the in situ application of a hernia mesh during minimally invasive surgery.

2. Background of Related Art

Meshes are used during both laparoscopic and open surgery for repair of many types of defects and or injuries. For example, surgical meshes are used as catheter and cannula cuffs, for vascular anastomosis reinforcement, as wound dressings, for chest wall closure, as urinary incontinence slings, and for repair of hernias. Surgical meshes are used to provide support to surrounding tissue and as a supplement to standard suturing.

Hernias that appear at the site of a prior surgical incision or due to a defect in the abdominal wall are often called ventral hernias. Ventral hernias typically occur when an organ protrudes through the muscular wall holding organs in place, often at the site of a previous incision. Any prior abdominal operation, where there is incomplete scar formation or healing of the tissue, may develop a ventral hernia.

Ventral hernias occur more commonly along a straight line from the xiphoid process of the breastbone down to the pubic bone, and are more complex in these regions. Ventral hernias in this area have a high rate of recurrence if repaired via a simple suture technique under tension. For this reason, it is especially advised that ventral hernias be repaired via a tension free repair method using a mesh.

Open surgical repairs of ventral hernias may be difficult and complicated operations. The weakened tissue of the abdominal wall is re-incised and during repair the weakened tissue may be reinforced using a prosthetic mesh. The large incision required to perform this surgery may lead to complications, such as infection. In addition, large incisions required for open repair are commonly associated with significant postoperative pain.

Minimally invasive surgery for ventral hernias has shown several benefits including quicker recovery and shorter hospital stays, as well as a significantly reduced risk of infection and hernia recurrence. These benefits are due to both the smaller incision size and the reduced amount of time required to perform the surgery as compared to open surgery.

Whether open or minimally invasive, the use of trans-abdominal suture knots and tacks to secure the mesh to the tissue may create significant postoperative pain. In the case of trans-abdominal sutures, the suture is sub-fascially knotted in place. These sub-fascial knots may be a significant source of post operative pain. At times, the sub-facial knot may be located over abdominal nerves causing additional pain. Therefore, methods and systems for reducing surgical time and use of sub-fascial knots or tacks are needed.

SUMMARY

The present disclosure includes a method of laparoscopic repair of a ventral hernia. The method may include providing a needle, a barbed suture having a distal end attached to the needle and surgical mesh. In embodiments, the barbed suture may be attached to the surgical mesh at a proximal end of the barbed suture. The surgical mesh, barbed suture, and needle may be rolled to form a rolled mesh with the needle oriented substantially parallel to a longitudinal x-axis of the rolled mesh. In embodiments, the barbed suture may be attached to the surgical mesh prior to rolling the mesh. In embodiments, the barbed suture may be attached to the surgical mesh through a loop at a proximal end of the barbed suture or with a suture tie at a proximal end of the barbed suture. The rolled mesh may then be transferred into a body cavity via a laparoscopic device. The laparoscopic device may be, for example, a trocar. Following transfer, the rolled mesh may be unrolled and laid under a ventral hernia in an abdominal wall. The needle and barbed suture may then be threaded through the surgical mesh and the abdominal wall and then the barbed suture may be trimmed. In embodiments, the threading step may include performing a second threading back along a path of the previous threading. In embodiments, the second threading may be perpendicular to a path of the previous threading.

The present disclosure also includes a hernia repair system. The hernia repair system may include a surgical mesh, a needle, and a barbed suture having a distal end attached to the needle and a proximal end attached to the surgical mesh. The surgical mesh may also include loops through which the needle may be threaded. In embodiments, the surgical mesh and barbed suture may be rolled to form a rolled mesh having a needle oriented substantially parallel to a longitudinal axis of the rolled mesh. The barbed suture and surgical mesh may be bioabsorbable and/or non-bioabsorbable. The barbed suture and/or surgical mesh may include a bioactive agent, such as, analgesics, antispasmodics, and/or anesthetics.

The present disclosure also includes a method of laparoscopic repair of a ventral hernia. The method may include providing a surgical mesh; providing a barbed suture having a proximal end attached to the surgical mesh; rolling the surgical mesh and the barbed suture to form a rolled mesh; transferring the rolled mesh into a body cavity via a laparoscopic device; unrolling and laying the surgical mesh under a ventral hernia in an abdominal wall; attaching a needle to the barbed suture; threading the needle and the barbed suture through the surgical mesh and the abdominal wall; and trimming the barbed suture. The threading step may include the step of performing a second threading back along a path of or perpendicular to a path of the previous threading. The laparoscopic device may be a trocar. The method can also include the step of attaching the barbed suture to the surgical mesh prior to the rolling step. The barbed suture may be attached at a proximal end of the barbed suture. The attachment may be through a loop at a proximal end of the barbed suture or with a suture tie at a proximal end of said barbed suture.

The disclosure also includes a hernia repair system including a surgical mesh; a barbed suture having a proximal end attached to the surgical mesh. The surgical mesh and the barbed suture may be rolled to form a rolled mesh. The barbed suture and surgical mesh may be bioabsorbable and/or non-bioabsorbable. The barbed suture and/or the surgical mesh may include a bioactive agent.

BRIEF DESCRIPTION OF DRAWINGS

The foregoing objects and advantages of the disclosure will become more apparent from the reading of the following description in connection with the accompanying drawings, in which.

DETAILED DESCRIPTION

Figure 1A:
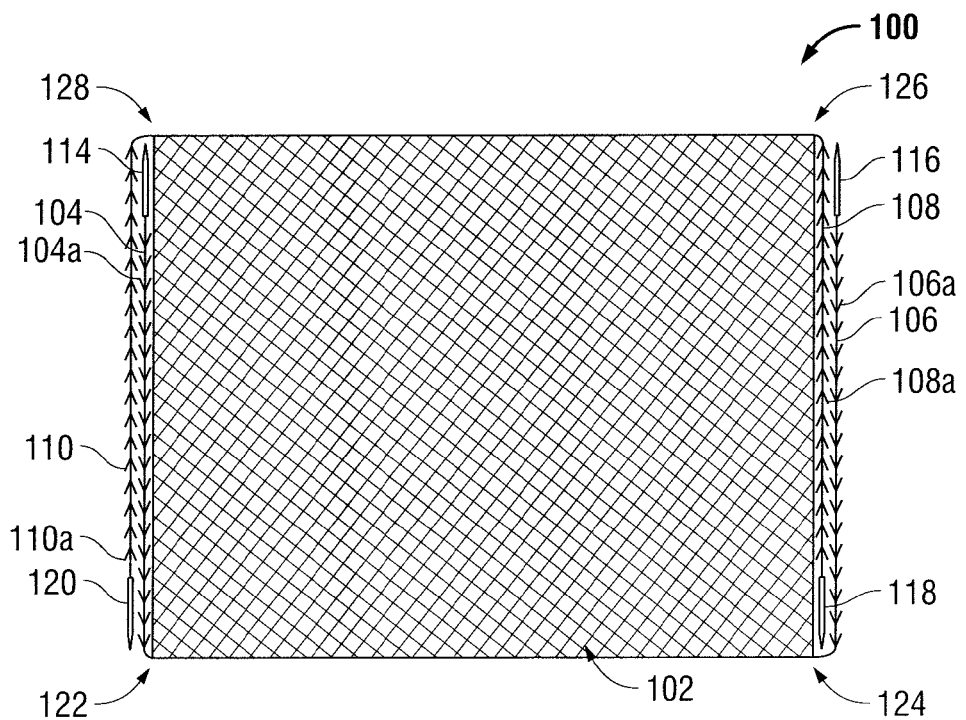
FIG. 1A illustrates an embodiment of a hernia repair system of the disclosure.

The present disclosure relates to devices, systems, and methods for minimally invasive surgeries such as, endoscopic, laparoscopic, arthroscopic, endoluminal and/or transluminal placement of a surgical mesh at a surgical site. As used herein the term "surgical mesh" is used to refer to any type of patch for use in surgical procedures, such as, for example, meshes that require suturing to the abdominal wall. Although described herein with reference to a ventral hernia mesh, the method of the disclosure may be used in any surgical repair. As used herein the term "laparoscopic deployment device" is used to refer to a deployment device that may be used during minimally invasive surgeries described above.

In the drawings and in the description that follows, the term "proximal," as is traditional, will refer to an end of a device that is closer to the user, while the term "distal" will refer to the end of the device that is further from the user.

Laparoscopic surgical procedures are minimally invasive procedures, which are carried out within the body cavity through use of access ports in conjunction with elongated surgical devices. An initial opening in the body tissue enables passage of the endoscopic or laparoscopic device to the interior of the body. Openings include natural passageways of the body or openings, which are created by a tissue piercing device such as a trocar. During laparoscopic procedures, narrow punctures or incisions are made minimizing trauma to the body cavity and reducing patient recovery time. Although described herein with reference to laparoscopic surgery, the method may be applied to any type of surgery.

Referring now in specific detail to the drawings, in which like numbers identify similar or identical elements, FIG. 1A illustrates an embodiment of a hernia repair system and is generally designated 100. The hernia repair system 100 includes a mesh 102, which is suitable for use in situ. The mesh 102 includes barbed sutures 104, 106, 108, and 110, each having respective barbs 104a, 106a, 108a, and 110a. Each barbed suture 104, 106, 108, and 110 includes a respective needle 114, 116, 118, and 120 attached to a distal end thereof The proximal end of each barbed suture 104, 106, 108, and 110 may be attached to the mesh 102 at respective fixation points 122, 124, 126, and 128.

Although illustrated with four barbed sutures and needles, any number of barbed sutures and needles sufficient to secure the mesh to the tissue may be included in the hernia repair system. In embodiments, there may be one barbed suture per corner. In other embodiments, there may be one barbed suture every 3 centimeters around the perimeter of the mesh. Still in other embodiments, where the mesh is non-rectangular (See FIG. 1B) i.e., triangular, circular, etc., there may be one barbed suture approximately every 3 centimeters around the perimeter of the mesh.

With continued reference to FIG. 1A, the barbed sutures 104, 106, 108, 110, may be attached to the mesh 102 immediately prior to performing the surgical procedure or may be attached to the mesh 102 during manufacturing.

Figure 1B:
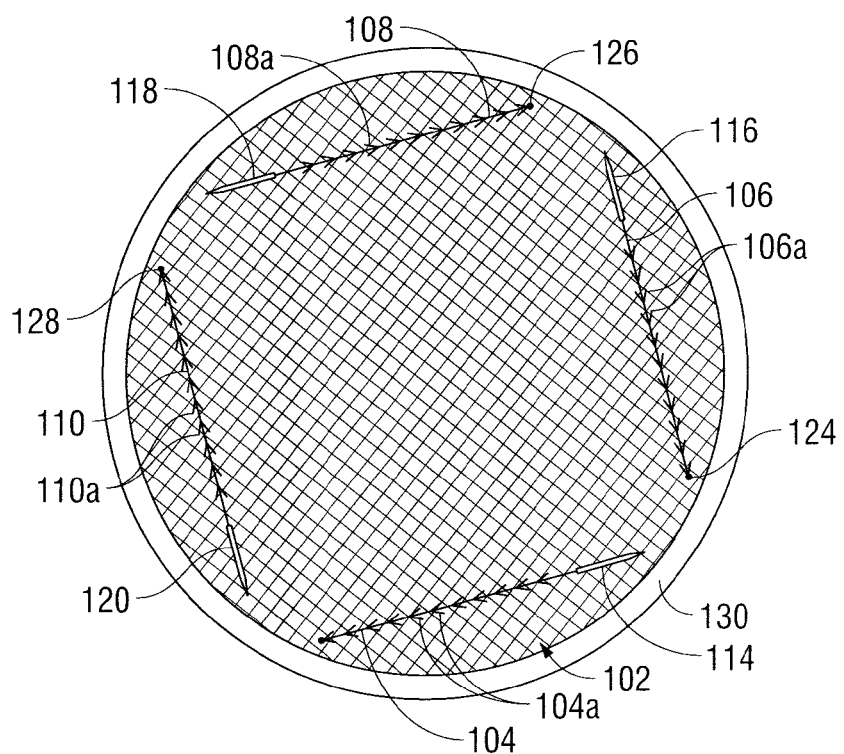
FIG. 1B illustrates another embodiment of a hernia repair system of the disclosure.

With reference to FIG. 1B, the barbed sutures 104, 106, 108, 110 may be aligned on the mesh in such a manner that barbs 104a, 106a, 108a, 110a secure, attach or stick respecting sutures 104, 106, 108, 110 to the mesh 102. Although barbed sutures 104, 106, 108, 110 are shown attached to respective needles 114, 116, 118, 120, in some embodiments, the barbed sutures do not include a needle affixed thereto. The mesh 102 may also include an anti-adhesion barrier 130 surrounding the edges of the mesh 102.

Figure 2A:
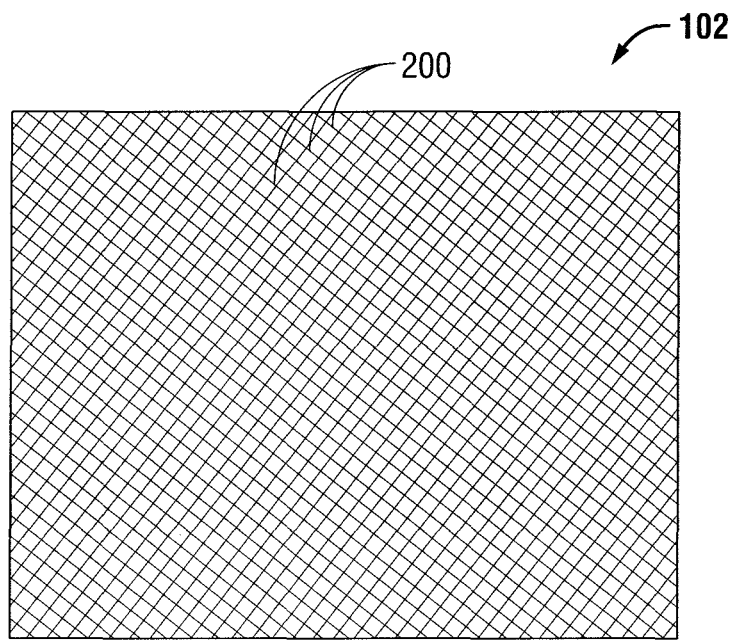
FIGS. 2A and 2B illustrate embodiments of a mesh of the hernia repair system of FIG. 1.
Figure 2B:
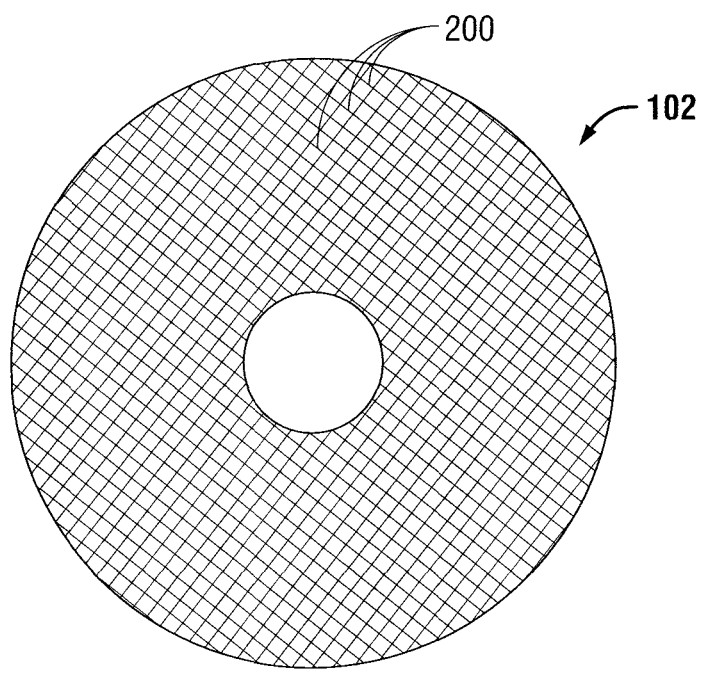

As shown in FIG. 2, the mesh 102 may be any type of mesh for use in surgical repair. Although shown as rectangular or circular in shape, the mesh 102 may be any suitable shape and may include one or more layers. Mesh 102 may be made of multiple fibers 200, or may be made of a single fiber. The fibers 200 may be a monofilament or multi-filament.

The fibers 200 forming the mesh 102 may be made from a natural material or a synthetic material. The fibers 200 may be biodegradable or non-biodegradable. It should of course be understood that any combination of natural, synthetic, bioadegradable and non-biodegradable materials may be used to form the fibers 200. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural biodegradable polymers include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers include polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like), dioxanones (e.g., 1,4-dioxanone and p-dioxanone), 1, dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the fibers 200 may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

The mesh 102 may be formed using any method suitable to forming mesh 102 structures, including but not limited to knitting, weaving, non-woven techniques, and the like. Suitable techniques for making the mesh are within the purview of those skilled in the art. In embodiments, the mesh 102 has a three dimensional structure, such as the knitted textiles described in U.S. Pat. Nos. 7,021,086 and 6,443,964 the entire contents of which are incorporated by reference herein.

In embodiments, the mesh 102 may be permanent, such as, for example, a polypropylene mesh. These types of meshs are available under the tradenames: PARIETEX™, PERMACOL™, and SURGIPRO™ manufactured by and commercially available from Tyco Healthcare Group LLP dba Covidien AG, Mansfield, Mass. The PERMACOL™ mesh may be used with or without a collagen coating. Another mesh that may be used is the PARIETENE™, mesh commercially available from Sofradim, Treivoux, France.

The mesh 102 may be any shape or size suitable for covering the herniated area and securing the mesh 102 to surrounding tissue. The mesh 102 may be preformed to a certain size, such as, for example, a 9 cm diameter round mesh or 50 cm×50 cm square mesh. In embodiments, the mesh 102 may be cut to a particular size and shape as needed.

Figure 3A:
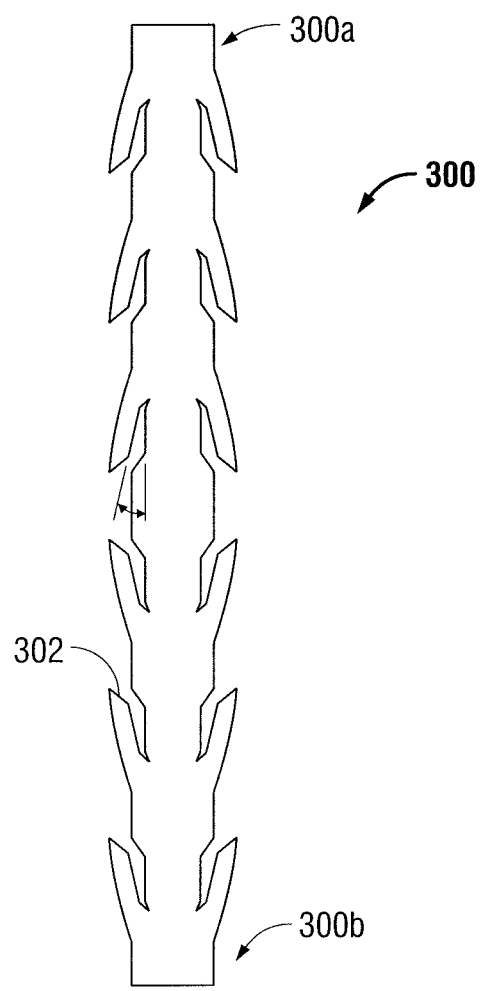
FIGS. 3A and 3B illustrate embodiments of a barbed suture of the hernia repair system FIG. 1.
Figure 3B:
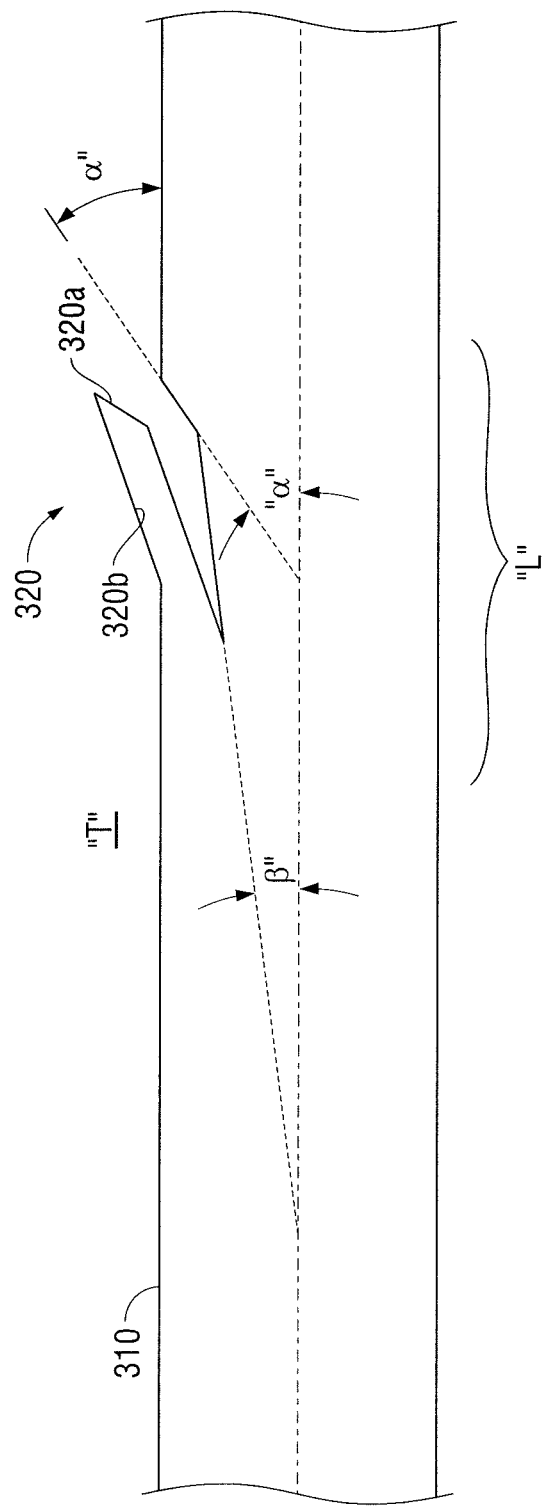

With reference to FIGS. 3A and 3B, barbed suture 300 may be similar to or the same as barbed sutures 104, 106, 108, 110.

For example, the suture can be made from a variety of polymers that may be biodegradable or non-biodegradable, such as those listed above for fibers 200. Biodegradable barbed sutures are described in U.S. patent application Ser. No. 11/556,002, filed Nov. 2, 2006, the entire content of which is incorporated herein by reference.

In embodiments, the barbed suture may include an elongated body having a barb, and first, second, and third portions being cut at first, second and third angles respective to a longitudinal axis of the elongated body to form the barb, i.e., a compound barbed suture. A compound barbed suture may be formed by providing a suture having a longitudinal axis and farming a compound barb along the suture wherein the compound barb defines an inner surface, which includes at least a first portion disposed at a first orientation relative to the longitudinal axis, a second portion disposed at a second orientation relative to the longitudinal axis, and a third portion disposed at a third orientation relative to the longitudinal axis. In embodiments, at least one of the first, second, and third portions may be substantially linear. In embodiments, at least one of the first, second, and third portions may be substantially non-linear.

In some embodiments, barbs may be formed by making acute angular cuts directly into the suture body, with cut portions pushed outwardly and separated from the body of the suture. The depth of the barbs thus formed in the suture body may depend on the diameter of the material and the depth of the cut.

As shown in FIG. 3B, the barbed suture may be a compound barb suture. The compound barb 320 includes two portions 320a, 320b which are disposed at two angles, α" and β" relative to a longitudinal axis A-A of the medical device. More specifically, the compound barb 320 includes a first portion 320a formed from the elongate body 310 at a first angle α", which is from about 0 degrees to about 90 degrees, in embodiments, from about 30 degrees to about 40 degrees, and in further embodiments, from about 31 degrees to about 38 degrees, relative to a longitudinal axis A-A of the elongate body 310. The second portion 320b is formed from the elongate body 310 at a second angle β" which is from about 0 degrees to about 90 degrees, in embodiments, from about 1 degree to about 10 degrees and in further embodiments, from about 1 degree to about 8 degrees relative to the longitudinal axis A-A of the elongate body 310.

The elongate body 310 of the barbed suture 300 is in direct contact with tissue "T". The elongate body 310 may be in direct contact with tissue "T" for any length "L" of the barbed suture 300 and is not limited to the contact length "L" as shown in FIG. 3B.

In embodiments, a method of forming a compound barb on a suture includes: forming a first cut in the suture, the first cut having a first ratio of cut depth to diameter of the suture; forming a second cut in the medical device the second cut having a second ratio of cut depth to diameter of the suture; and forming a third cut in the medical device, the third cut having a third ratio of cut depth to diameter of the suture.

In embodiments, the compound barb 320 and elongated body (suture) 310 and a first ratio of cut depth, which is approximately 1% to about 40%, and in certain embodiments, about 10% to about 30% of the diameter of the elongate body 310.

Compound barbs 320 may include a first ratio of cut depth, which is approximately 1% to about 40%, and in certain embodiments, about 10% to about 30% of the diameter of the elongate body 310. Compound barb 320 may include a second ratio of cut depth of approximately 5% to about 50%, and in certain embodiments, about 15% to about 45% of the diameter of elongated body 310. Compound barb 320 may include a third ratio of cut depth of approximately 15% to about 50%, and in some embodiments, from about 30% to about 50% the diameter of elongated body 14. In one embodiment, a plurality of barbs are formed at successive intervals along the longitudinal axis of the suture 300.

The compound barbed suture of FIG. 3B may be formed, for example, using a cutting element. The cutting element may generate ultrasonic energy, which is converted to mechanical energy by the cutting element. This mechanical energy causes displacement of the tool at an ultrasonic frequency powered by an ultrasonic generator. The ultrasonic frequency may range in embodiments from about 1 kHz to about 100 kHz; from about 10 kHz to about 90 kHz; or from about 15 kHz to about 50 kHz. The ultrasonic signal amplitude may range from about 1μ to about 125μ; in embodiments from about 15μ to about 60μ.

The ratio of the cut depth and the angle of the barbs relative to the suture are variable based on the signal amplitude of ultrasonic energy applied to the cutting element. For example, as the ultrasonic amplitude is increased, the ratio of the cut depth to the diameter and the angle of the barbs are decreased. As the ultrasonic amplitude is decreased, the ratio of the cut is increased. The method described above as well as the cutting element are described in U.S. patent application Ser. No. 12/178,361 filed Jul. 23, 2008, the entire content of which is incorporated herein by reference.

As shown in FIGS. 3A and 3B, an embodiment of a barbed suture capable of use with the aspects of the present disclosure is shown generally as suture 300. Although shown as a monofilament thread, it is envisioned that suture 300 may be formed from braided threads, multifilament threads and the like.

Although shown having a circular cross-sectional geometry, the cross-sectional geometry of suture 300 may be of any suitable shape.

With continued reference to FIGS. 3A and 3B, barbed suture 300 may be formed using any technique within the purview of those skilled in the art, such as, for example, extrusion, molding and/or solvent casting. In some embodiments, suture 300 may include a yarn made of more than one filament, which may contain multiple filaments of the same or different materials. Where suture 300 is made of multiple filaments, suture 300 may be made using any known technique such as, for example, braiding, weaving or knitting. Filaments may also be combined to produce a non-woven suture. Suture 300 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

Suture 300 includes a plurality of barbs 302 formed along a length thereof Barbs 302 are radially and longitudinally spaced along suture 300 and may be formed using any suitable method. Barbs 302 on suture 300 may extend in the same direction along the entire length thereof, or may instead extend in one direction on a first half of suture 300 and may extend in an opposite direction on a second half of suture 300. Proximal end 300a, or distal end 300b, of suture 300 may include a sharpened tip or needle (not shown) configured for penetrating tissue. The needle may be any surgical needle as are known to those of skill in the art. In embodiments, the needle may be a straight needle. Either or both ends 300a, 300b of suture 300 may include a fixation device (not shown). Non-limiting examples of suitable fixation devices 306 include surgical pins, screws, suture anchors, nails, and the like. In embodiments, the suture 300 may be attached to the mesh 100 by looping the barbed suture through the mesh. A barbed suture such as is disclosed in U.S. patent application Ser. No. 12/361,962, filed Jan. 29, 2009, the entire content of which is incorporated herein by reference. A compound barbed suture is available commercially as V-LOC™ from Tyco Healthcare Group, LLP (dba Covidien AG, Mansfield, Mass.).

Either or both of the mesh and barbed suture may include a bioactive agent. The bioactive agent may be added to the barbed suture as disclosed in U.S. application Ser. No. 11/899,852, filed Sep. 6, 2007, the entire content of which is incorporated by reference herein. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the mesh or barbed suture in any suitable form, e.g., films, powders, liquids, gels, and the like.

Examples of classes of bioactive agents, which may be utilized in accordance with the present disclosure include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the mesh and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent include: triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil, nonoxynol 9, fusidic acid, cephalosporins; and combinations thereof. In addition, antimicrobial proteins and peptides such as bovine lactoferrin and lactoferricin B may be included as a bioactive agent.

Other bioactive agents, which may be included as a bioactive agent include local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the mesh or suture include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor;, colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

Figure 4:
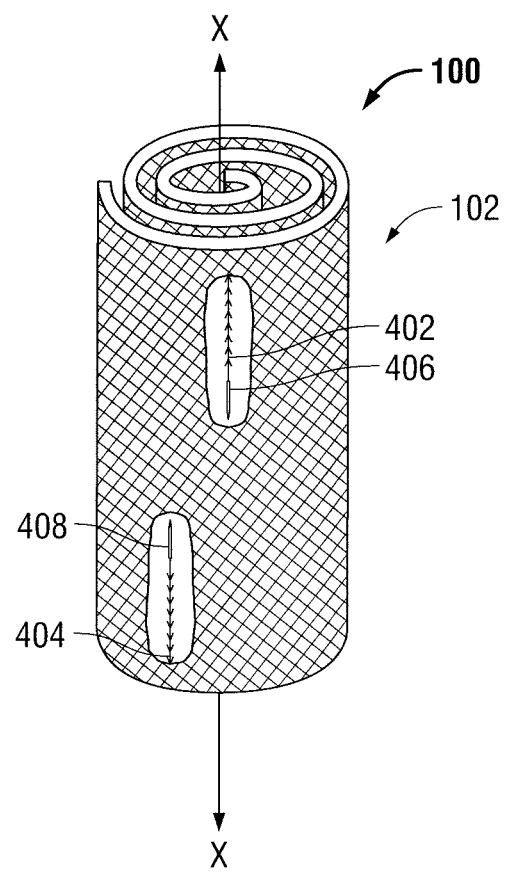
FIG. 4 illustrates an embodiment of a mesh of the hernia repair system of FIG. 1.

With reference to FIG. 4 mesh 102 of the hernia repair system 100 may be rolled with barbed sutures 402, 404 such that respective needles 406, 408 thereof may be oriented parallel to a longitudinal X-axis of mesh 102. Barbed sutures 402, 404 may be similar to or the same as barbed sutures 102, 104, 106, 108, and/or 300. Barbed sutures 402, 404, may be attached to mesh 102 at fixation points (not shown) in a manner as described above. For example, by looping barbed sutures 402, 404 through mesh 102, or with a fixation device. Needles 406, 408 may be similar to or the same as needles 114, 116, 118, 120. Any number of barbed sutures and needles may be oriented along a longitudinal x-axis of the rolled mesh 102. In embodiments, the needles may be threaded through the mesh 102 along the longitudinal X-axis of the rolled mesh 102 to secure the needles during transport.

Rolling, folding, or otherwise orienting the mesh with the barbed sutures and needles parallel to the longitudinal x-axis of the rolled mesh 102 forms a shape more suitable for transfer through a laparoscopic device during laparoscopic surgery. Laparoscopic devices are known in the art and include, for example, the devices disclosed in U.S. Patent Application Publication No. 2006/0229640, filed Mar. 29, 2005; U.S. Patent Application Publication No. U.S. 2006/0200170, filed Mar. 7, 2005; and U.S. Patent Application Publication No. 2006/0200169, filed Mar. 7, 2005, the entire contents of which are incorporated by reference herein.

The hernia repair system of the present disclosure provides a single system for transfer of needles, sutures, and mesh needed to perform repair of the hernia. This reduces the time required for separate insertion of each of these tools. Instead, the surgeon may insert the hernia repair system, unroll the mesh, thread the barbed sutures through the abdominal wall where the barbs of the suture may grip the rectus abdominal muscle, and cut the sutures. The traditional use of two sutures per fixation point may be replaced by the use of one barbed suture. There is no need for separate attachment and knotting of the suture to the mesh. This may reduce the time required to complete the surgical procedure. Additionally, the barbed sutures unidirectionally secure the mesh to the tissue, i.e., the barbs prevent the suture from movement in the direction opposite the direction of their insertion. Accordingly, the mesh may be secured to the tissue by the barbed suture and there may be no need for knotting or tacking of the suture.

Trans-abdominal suture knots and tacks used to secure meshes to tissue may create significant postoperative pain. In the case of trans-abdominal sutures, the suture is sub-fascially knotted in place. These sub-fascial knots may be a significant source of post-operative pain. At times, the sub-facial knot may be located over abdominal nerves causing additional pain. Use of the hernia repair system of the present disclosure prevents the need for sub-fascial and/or trans-abdominal suture knots, thereby eliminating post-operative pain caused by these knots.

Figure 5A:
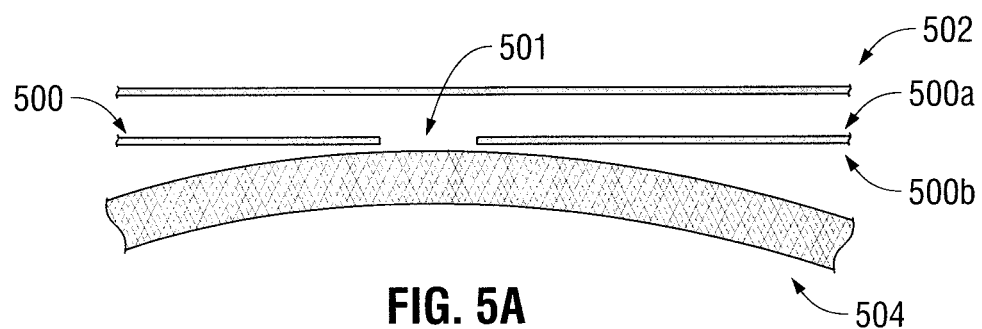
FIG. 5A is a schematic illustration of a tear in an abdominal wall.
Figure 5B:
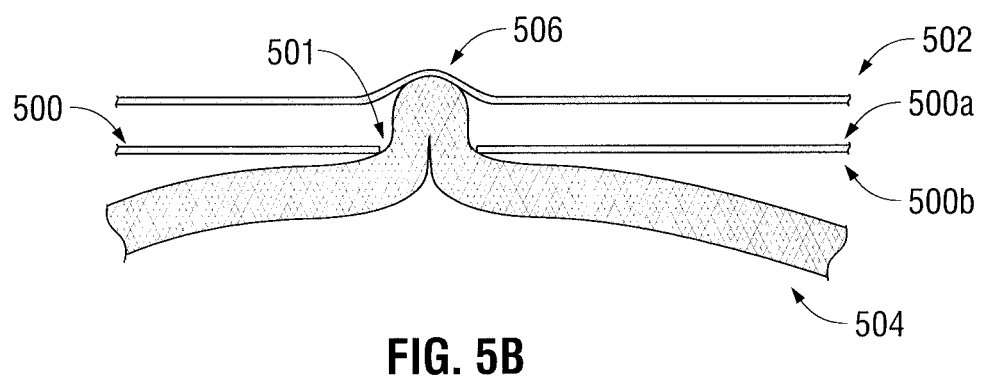
FIG. 5B is a schematic illustration of a ventral hernia.

Referring now to FIGS. 5A-5E, a method of using hernia repair system 100 to perform a surgical repair procedure is shown and described. With reference to FIG. 5A, a ventral hernia may involve a tear 501, in the abdominal wall 500. Abdominal wall 500 is defined by an external side 500a and internal side 500b. A surface tissue 502, which covers the external side 500a of abdominal wall 500, may or may not be immediately effected by this tear 501. An internal organ 504 located below the internal side 500b of the abdominal wall 500 may not protrude until some form of exertion or use of the muscle located at the abdominal wall 500 forces the internal organ 504 into the tear 501. Depending on the size and location of the tear 501, exertion may not be needed to cause the organ to protrude. As shown in FIG. 5B, a hernia occurs when internal organ 504 protrudes into the tear 501 of abdominal wall 500. Oftentimes the protrusion creates a bulge 506 in the surface tissue 502.

Figure 5C:
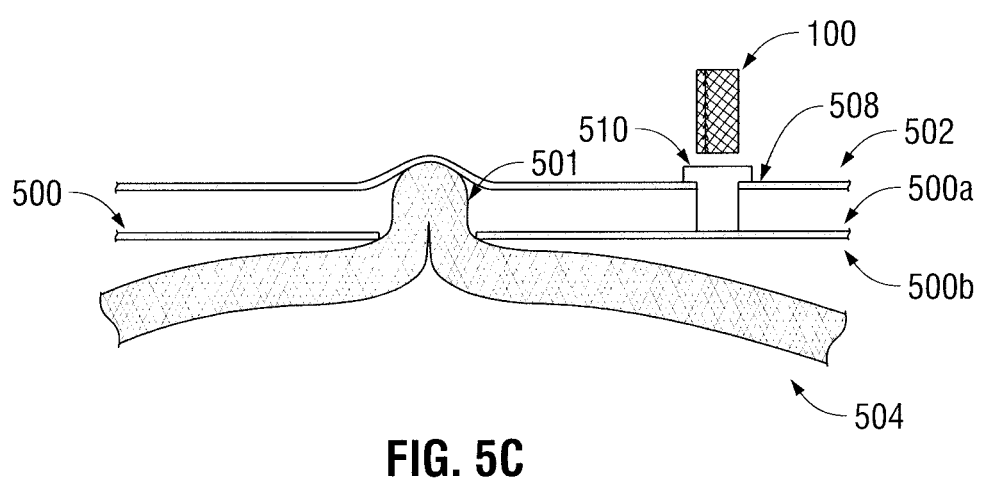
FIG. 5C is a schematic illustration of an incision and laparoscopic transfer of a hernia repair system of the disclosure.
Figure 5D:
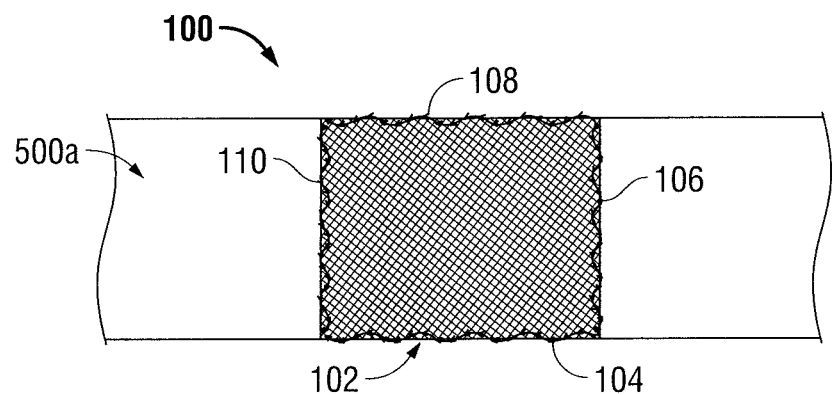
FIG. 5D is a schematic illustration of an abdominal wall during repair with the hernia repair system of the disclosure.
Figure 5E:
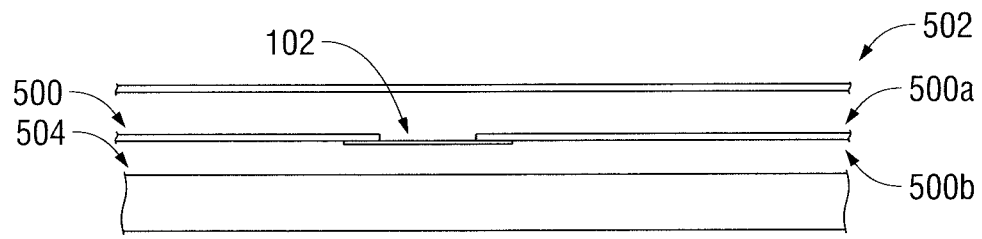
FIG. 5E is a schematic illustration of a tear in an abdominal wall following repair with the hernia repair system of the disclosure.

In order to correct the defect, as depicted in FIG. 5C, an incision 508 may be made through surface tissue 502 and/or abdominal wall 500 in close proximity to tear 501 and a hernia repair system 100, including rolled mesh 102 as described above, may be inserted using trocar 510 or similar laparoscopic device. As shown in FIG. 5D, the hernia repair system 100 is unrolled and placed above tear 501 on external side 500a of abdominal wall 500. In other embodiments, hernia repair system 100 may be placed beneath tear 501 on internal side 500b of abdominal wall. In still other embodiments, a hernia repair system 100 may be positioned above and below tear 501 on both sides of abdominal wall 500. The needles (not shown) may be used to thread barbed sutures 104, 106, 108, 110 through the mesh 102 and the abdominal wall 500. As depicted in FIG. 5E hernia repair system 100 seals abdominal wall 500 returning internal organ 504 to its original location and repairing protrusion 506.

Figure 6A:
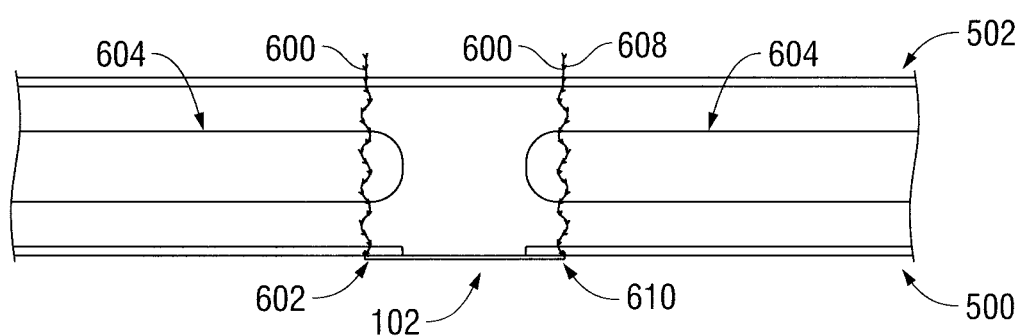
FIGS. 6A and 6B are schematic illustrations depicting various methods for securing the mesh with barbed sutures in accordance with the present disclosure.
Figure 6B:
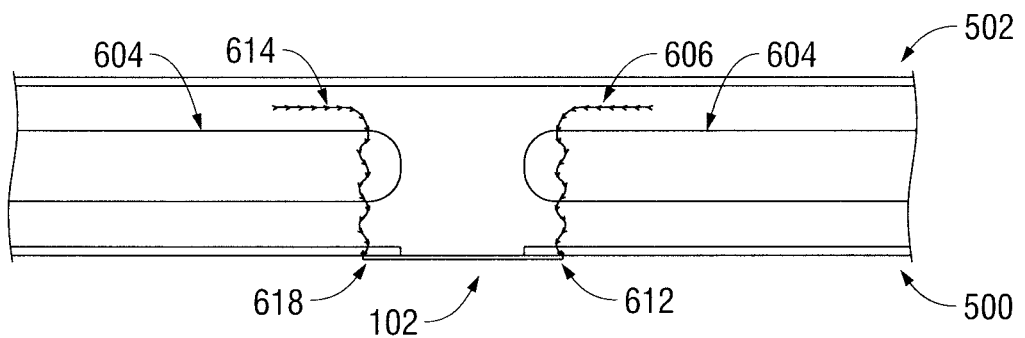

As shown in FIGS. 6A and 6B, various methods of securing the mesh 102 to the peritoneum 500b of the abdominal wall 500 with a barbed suture 600 may be used by the surgeon. As shown in FIG. 6A, the surgeon may thread the barbed sutures 600, 608 from respective fixation points 602, 610, into the abdominal wall 500, through the rectus muscle 604, and through the surface tissue 502. In embodiments, as shown in FIG. 6B, barbed sutures 606, 614, may be threaded from respective fixation points 612, 618 into the abdominal wall 500, through the rectus muscle 604, and then threaded at an angle under the surface tissue 502. Although shown at an angle of 90 degrees in FIG. 6B, the barbed suture may be angled in any direction.

Figure 7A:
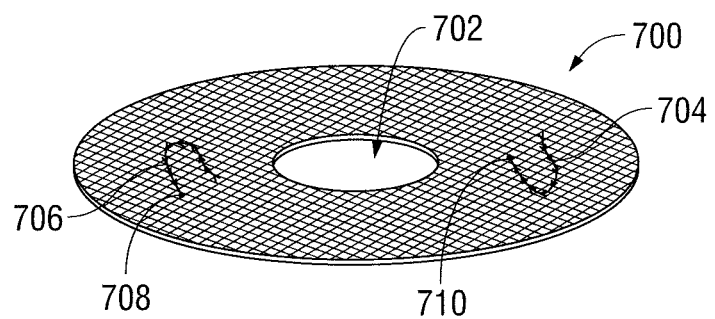
FIG. 7A illustrates another embodiment of a hernia repair system.
Figure 7B:
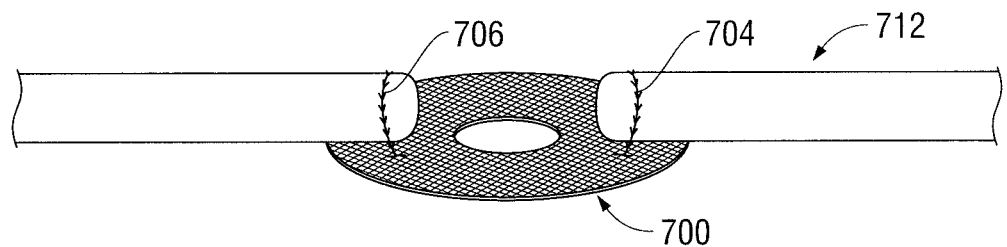
FIG. 7B is a schematic illustration showing a repair of an umbilical hernia with the hernia repair system of FIG. 7A.

Depicted in FIGS. 7A and 7B, is a mesh 700 for repair of umbilical hernias. The mesh 700 includes a central opening 702. Barbed sutures 704, 706 may be attached to the umbilical mesh at attachment points 708, 710, respectively around opening 702. The mesh 700 may be secured beneath the abdominal wall 712 and barbed sutures 704, 706 may be pulled through the abdominal wall 712, thereby securing the mesh 700 to the abdominal wall 712.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

We claim:

1. A method of laparoscopic repair of a ventral hernia, comprising the steps of:
    a. providing a needle;
    b. providing a barbed suture having a distal end attached to said needle;
    c. providing a surgical mesh;
    d. rolling said surgical mesh, said barbed suture, and said needle to form a rolled mesh having said needle positioned within a perimeter of said rolled mesh and oriented substantially parallel to a longitudinal axis of said rolled mesh;
    e. transferring said rolled mesh into a body cavity via a laparoscopic device;
    f. unrolling and laying said surgical mesh under a ventral hernia in an abdominal wall;
    g. threading said needle and barbed suture through said surgical mesh and said abdominal wall; and
    h. trimming said barbed suture.

2. The method according to claim 1, wherein the threading step further comprises the step of performing a second threading back along a path of the previous threading.

3. The method according to claim 1, wherein the threading step further comprises the step of performing a second threading perpendicular to a path of the previous threading.

4. The method according to claim 1, wherein said laparoscopic device is a trocar.

5. The method according to claim 1, further comprising the step of attaching said barbed suture to said surgical mesh prior to said rolling step.

6. The method according to claim 5, further comprising the step of attaching said barbed suture to said surgical mesh at a proximal end of said barbed suture.

7. The method according to claim 5, further comprising the step of attaching said barbed suture to said surgical mesh through a loop at a proximal end of said barbed suture.

8. The method according to claim 5, further comprising the step of attaching said barbed suture to said surgical mesh with a suture tie at a proximal end of said barbed suture.

9. The method according to claim 1, wherein the step of rolling the mesh further includes threading the needle through the mesh along the longitudinal X-axis of the rolled mesh to secure the needle during transport.

10. A method of laparoscopic repair of a ventral hernia, comprising the steps of:
    a. providing a barbed suture having a distal end attached to a needle;
    b. attaching said barbed suture to a surgical mesh through a loop at a proximal end of said barbed suture;
    c. rolling said surgical mesh and said barbed suture to form a rolled mesh having said needle oriented substantially parallel to a longitudinal axis of said rolled mesh;
    d. transferring said rolled mesh into a body cavity via a laparoscopic device;
    e. unrolling and laying said surgical mesh under a ventral hernia in an abdominal wall;
    f. threading said needle and barbed suture through said surgical mesh and said abdominal wall; and
    g. trimming said barbed suture.

* * * * *